United States Patent
Pai et al.

(10) Patent No.: US 11,578,038 B2
(45) Date of Patent: Feb. 14, 2023

(54) METHOD FOR PREPARING POLYTHIOL COMPOSITION

(71) Applicant: SKC CO., LTD., Gyeonggi-do (KR)

(72) Inventors: Jaeyoung Pai, Gyeonggi-do (KR); Seung Mo Hong, Gyeonggi-do (KR); Hyeon Myeong Seo, Gyeonggi-do (KR); Junghwan Shin, Gyeonggi-do (KR); Jeongmoo Kim, Gyeonggi-do (KR); Jung Hwan Myung, Gyeonggi-do (KR); Hyuk Hee Han, Gyeonggi-do (KR)

(73) Assignee: SKC CO., LTD., Gyeonggi-do (KR)

( * ) Notice: Subject to any disclaimer, the term of this patent is extended or adjusted under 35 U.S.C. 154(b) by 0 days.

(21) Appl. No.: 17/117,407

(22) Filed: Dec. 10, 2020

(65) Prior Publication Data

US 2021/0179552 A1    Jun. 17, 2021

(30) Foreign Application Priority Data

Dec. 13, 2019  (KR) .................. 10-2019-0166924
Dec. 13, 2019  (KR) .................. 10-2019-0166980

(51) Int. Cl.
*C07C 319/14* (2006.01)
*C07C 323/12* (2006.01)

(52) U.S. Cl.
CPC .......... *C07C 319/14* (2013.01); *C07C 323/12* (2013.01)

(58) Field of Classification Search
CPC .... C07C 319/14; C07C 321/14; C07C 323/12
See application file for complete search history.

(56) References Cited

U.S. PATENT DOCUMENTS

| | | | |
|---|---|---|---|
| 2015/0126781 A1* | 5/2015 | Kawaguchi et al. | C07C 319/14 |
| 2016/0229798 A1 | 8/2016 | Nishimori et al. | |
| 2018/0282270 A1* | 10/2018 | Shin | C08G 18/3876 |
| 2019/0062270 A1* | 2/2019 | Kageyama et al. | C07C 319/14 |
| 2019/0292144 A1* | 9/2019 | Hong et al. | C07C 321/14 |

FOREIGN PATENT DOCUMENTS

| | | |
|---|---|---|
| EP | 2853527 A1 | 4/2015 |
| JP | 1990-270859 A | 11/1990 |
| JP | 2015086204 A | 5/2015 |
| JP | 2019-172630 A | 10/2019 |
| KR | 10-2012-0058635 A | 6/2012 |
| KR | 10-2014-0141723 A | 12/2014 |
| KR | 10-2018-0024561 A | 3/2018 |

OTHER PUBLICATIONS

Agilent Technologies ("An Introduction to Gel Permeation Chromatography and Size Exclusion Chromatography", Dec. 2016, https://www.agilent.com/library/primers/Public, pp. 1-32), (Year: 2016).*
Waters Corporation ("Introduction to GPC, Columns, Distributions, Sample Prep., Calibration, What's New", http://www.tainstruments.com/uploads/GPC_G, 2018, pp. 1-69). (Year: 2018).*
U.S. Appl. No. 17/048,743, filed Oct. 19, 2020 (Year: 2020).*
Extended European Search Report issued by the European Patent Office dated Sep. 30, 2021.

* cited by examiner

Primary Examiner — Rosalynd A Keys
(74) Attorney, Agent, or Firm — IP & T Group LLP

(57) ABSTRACT

The embodiments relate to a process for preparing a polythiol composition, which comprises reacting a halogen compound or an alcohol compound with thiourea to prepare a thiouronium salt solution; and adding a basic solution to the thiouronium salt solution to hydrolyze it. The hydrolysis reaction is terminated when the area of peak A in the graph measured by gel permeation chromatography of the reactant in the hydrolysis step under certain conditions is 0.5% to 8% based on the total peak area. A tetrafunctional polythiol composition having high purity can be obtained. Thus, an optical lens having excellent color, transparency, and refractive index can be obtained.

8 Claims, 2 Drawing Sheets

[Fig. 1]
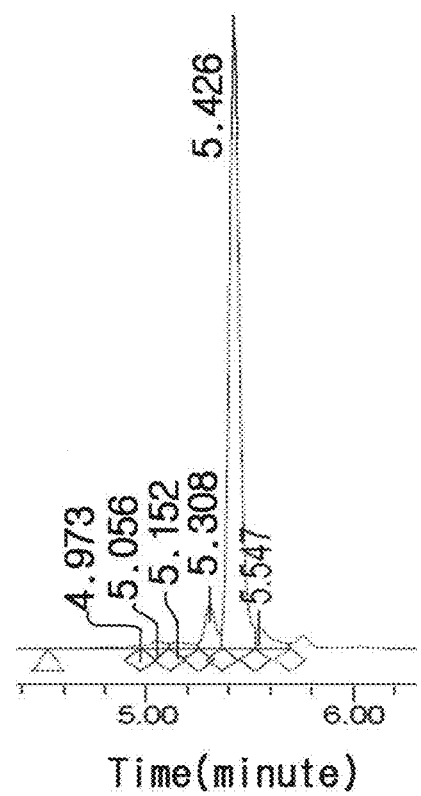
[Fig. 2]
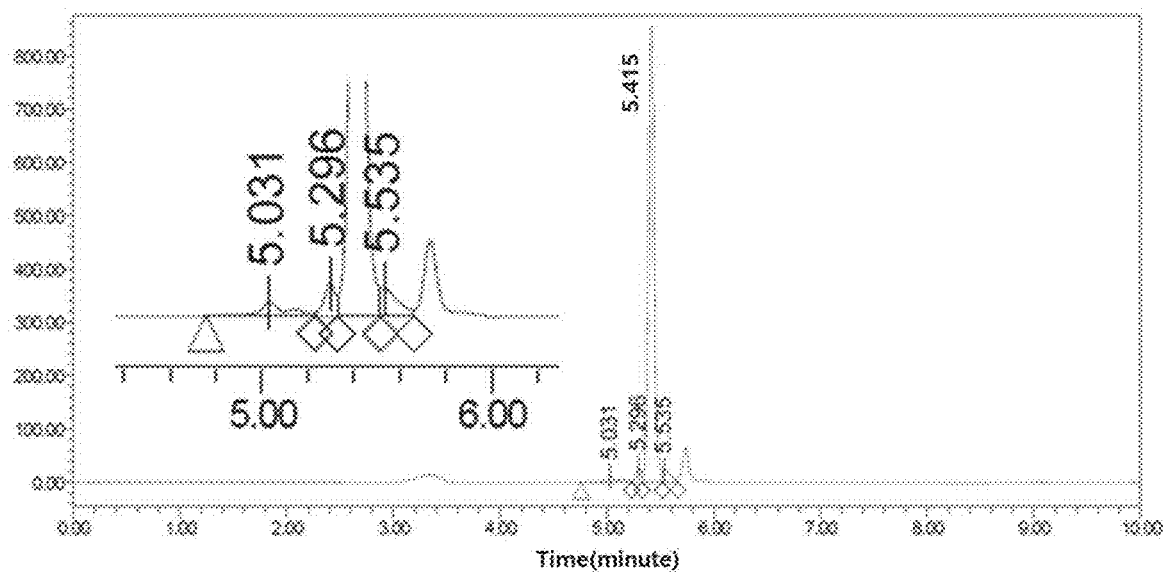

[Fig. 3]
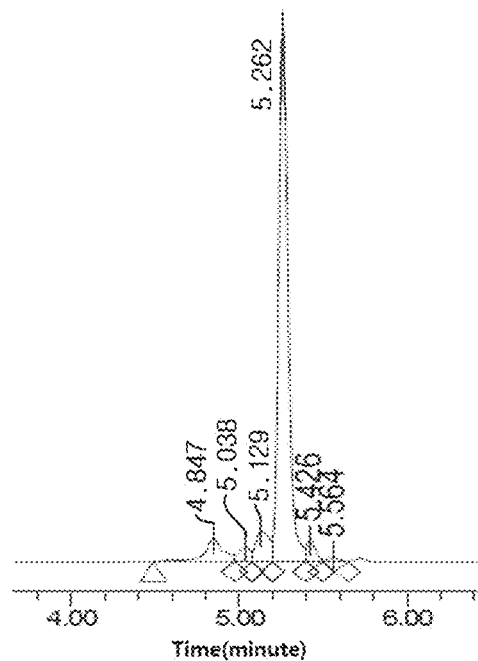
[Fig. 4]
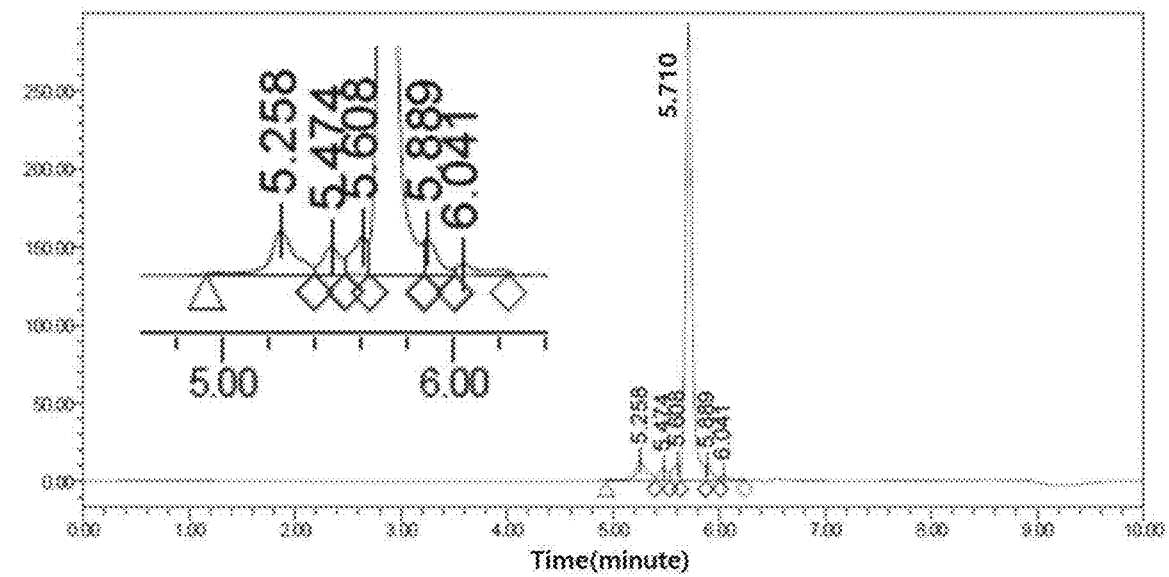

METHOD FOR PREPARING POLYTHIOL COMPOSITION

The present application claims priority of Korean patent application number 10-2019-0166924, and 10-2019-0166980 filed on Dec. 13, 2019. The disclosure of each of the foregoing applications is incorporated herein by reference in its entirety.

TECHNICAL FIELD

Embodiments relate to a process for preparing a polythiol composition capable of providing a trifunctional polythiol composition and a tetrafunctional polythiol composition with high purity, from which an optical lens having excellent color, transparency, and refractive index can be obtained.

BACKGROUND ART

Since optical materials using plastics are lightweight, hardly breakable, and excellent in dyeability as compared with optical materials made of inorganic materials such as glass, they are widely used as optical materials for eyeglass lenses, camera lenses, and the like. Among them, optical materials prepared from a polythiourethane-based polymer obtained by polymerizing a polythiol compound and a polyisocyanate compound are widely used by virtue of their excellent physical properties such as high refractive index, high Abbe's number, and high strength.

In order to enhance the physical properties of such an optical material, research is ongoing on enhancements in the purity of a polythiol compound that affects the physical properties of a polythiourethane-based compound. For example, Japanese Laid-open Patent Publication No. 1990-270859 discloses a process for preparing a polythiol compound by reacting 2-mercaptoethanol with epichlorohydrin, reacting the resultant with thiourea to obtain an isothiouronium salt, and hydrolyzing it. However, there are still impurities generated by side reactions.

DETAILED DESCRIPTION OF THE INVENTION

Technical Problem

Accordingly, the embodiments aim to provide a process for preparing a polythiol composition capable of providing a trifunctional polythiol composition and a tetrafunctional polythiol composition with high purity, from which an optical lens having excellent color, transparency, and refractive index can be obtained.

Solution to the Problem

The process for preparing a polythiol composition according to an embodiment comprises reacting a halogen compound or an alcohol compound with thiourea to prepare a thiouronium salt solution; and adding a basic solution to the thiouronium salt solution to hydrolyze it, wherein the hydrolysis reaction is terminated when the area of peak A in the graph measured by gel permeation chromatography of the reactant in the hydrolysis step is 0.5% to 8% based on the total peak area.

Here, peak A is a peak located at −0.37 minute±0.08 minute with respect to the maximum peak (peak B) in the graph. The gel permeation chromatography is carried out under the conditions that tetrahydrofuran is used as the mobile phase, two columns are connected in series, the columns each having a length of 145 mm to 155 mm, a diameter of 4.5 mm to 4.7 mm, a pore size of 44 Å to 46 Å, and a particle diameter of 1.6 μm to 1.8 μm, the flow rate is 0.45 ml/minute to 0.55 ml/minute, and the injection amount is 9.5 μl to 10.5 μl.

The polythiol composition according to an embodiment comprises a polythiol represented by the following Formula 1, wherein the area of peak A in the graph measured by gel permeation chromatography of the entire composition is 0.5% to 8% based on the total peak area:

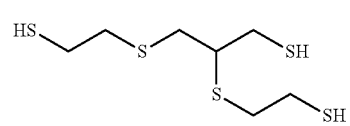

[Formula 1]

Here, peak A is a peak located at −0.37 minute±0.08 minute with respect to the maximum peak (peak B) in the graph. The conditions for the gel permeation chromatography are as described above.

The polymerizable composition according to an embodiment comprises a polythiol composition, and an isocyanate-based compound, wherein the polythiol composition comprises a trifunctional polythiol represented by the above Formula 1, wherein the area of peak A in the graph measured by gel permeation chromatography of the polythiol composition is 0.5% to 8% based on the total peak area. Here, peak A is a peak located at −0.37 minute±0.08 minute with respect to the maximum peak (peak B) in the graph. The conditions for the gel permeation chromatography are as described above.

The process for preparing a polythiol composition according to an embodiment comprises reacting a halogen compound or an alcohol compound with thiourea to prepare a thiouronium salt solution; and adding a basic solution to the thiouronium salt solution to hydrolyze it, wherein the hydrolysis reaction is terminated when the area of peak A in the graph measured by gel permeation chromatography of the reactant in the hydrolysis step is 0.5% to 8% based on the total peak area.

Here, peak A is a peak located at −0.4 minute±0.15 minute with respect to the maximum peak (peak B) in the graph. The gel permeation chromatography is carried out under the conditions that tetrahydrofuran is used as the mobile phase, two columns are connected in series, the columns each having a length of 145 mm to 155 mm, a diameter of 4.5 mm to 4.7 mm, a pore size of 44 Å to 46 Å, and a particle diameter of 1.6 μm to 1.8 μm, the flow rate is 0.45 ml/minute to 0.55 ml/minute, and the injection amount is 9.5 μl to 10.5 μl.

The polythiol composition according to an embodiment comprises a polythiol represented by the following Formula 2, wherein the area of peak C in the graph measured by gel permeation chromatography of the entire composition is 0.5% to 8% based on the total peak area:

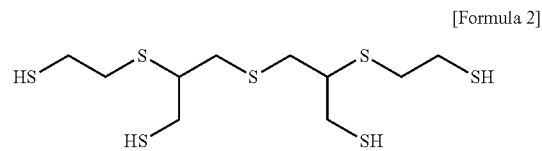 [SMILES: SCCSC(CS)CSCC(CS)SCCS]

[Formula 2]

Here, peak C is a peak located at −0.4 minute±0.15 minute with respect to the maximum peak (peak D) in the graph. The conditions for the gel permeation chromatography are as described above.

The polymerizable composition according to an embodiment comprises a polythiol composition; and an isocyanate-based compound, wherein the polythiol composition comprises a tetrafunctional polythiol represented by the above Formula 2, wherein the area of peak C in the graph measured by gel permeation chromatography of the polythiol composition is 0.5% to 8% based on the total peak area. Here, peak C is a peak located at −0.4 minute±0.15 minute with respect to the maximum peak (peak D) in the graph. The conditions for the gel permeation chromatography are as described above.

The optical lens according to an embodiment is prepared by thermally curing the polymerizable composition.

Advantageous Effects of the Invention

The process for preparing a polythiol composition according to an embodiment is capable of providing a trifunctional polythiol composition and a tetrafunctional polythiol composition with high purity. Thus, a polythiourethane prepared from the polythiol composition with high purity is excellent in transparency and refractive index. They can be advantageously used for preparing various plastic optical materials such as eyeglass lenses and camera lenses.

BRIEF DESCRIPTION OF THE DRAWINGS

FIGS. 1 to 4 are graphs obtained by performing gel permeation chromatography on the polythiol compositions of Examples 1 to 4.

BEST MODE FOR CARRYING OUT THE INVENTION

Hereinafter, the present invention will be described in detail with reference to the embodiments. The embodiments are not limited to those described below. Rather, they may be modified into various forms as long as the gist of the invention is not altered.

Throughout the present specification, when a part is referred to as "comprising" an element, it is understood that other elements may be comprised, rather than other elements are excluded, unless specifically stated otherwise.

All numbers and expression related to the quantities of components, reaction conditions, and the like used herein are to be understood as being modified by the term "about," unless otherwise indicated.

Process for Preparing a Polythiol Composition

The present invention provides a process for preparing a polythiol composition comprising a trifunctional polythiol compound with high purity (hereinafter, "trifunctional polythiol composition") and a polythiol composition comprising a tetrafunctional polythiol compound with high purity (hereinafter, "tetrafunctional polythiol composition").

Process for Preparing a Trifunctional Polythiol Composition

The process for preparing a trifunctional polythiol composition according to an embodiment comprises reacting a halogen compound or an alcohol compound with thiourea to prepare a thiouronium salt solution; and adding a basic solution to the thiouronium salt solution to hydrolyze it.

The process for preparing a polythiol composition according to an embodiment comprises reacting a halogen compound or an alcohol compound with thiourea to prepare a thiouronium salt solution.

First, in the step of preparing a thiouronium salt solution, a halogen compound and an alcohol compound are reacted to prepare a trifunctional polyol compound.

In this step, the alcohol compound may be reacted in an amount of 0.5 to 3 equivalents, 1 to 3 equivalents, 1.5 to 3 equivalents, or 2 to 3 equivalents, based on 1 equivalent of the halogen compound. For example, the halogen compound and the alcohol compound may be reacted at an equivalent ratio of 1:2.

In such event, a metallic catalyst such as sodium hydroxide or potassium hydroxide may be used as a reaction catalyst. The catalyst may be used in an amount of 0.5 to 2 equivalents, or 0.5 to 1 equivalent, based on 1 equivalent of the halogen compound.

The halogen compound may comprise F, Cl, Br, I, and the like. For example, it may be epichlorohydrin, but it is not limited thereto. The alcohol compound may be, for example, 2-mercaptoethanol, but it is not limited thereto.

Next, the trifunctional polyol may be reacted with thiourea under an acidic condition to prepare an isothiouronium salt. More specifically, the reaction may be carried out under reflux.

The thiourea may be used in an amount of 3 moles or more based on 1 mole of the alcohol compound. For example, the thiourea may be used in an amount of 3 moles to 6 moles, or 4.6 moles to 5 moles, based on 1 mole of the alcohol compound.

For the acidic condition, a hydrochloric acid solution, hydrogen chloride gas, or the like may be used. The type of the acidic substance to be used is not particularly limited as long as the reaction can be sufficiently carried out. For example, the use of hydrogen chloride may secure a sufficient reaction rate and prevent the coloring of the product. In addition, the acidic substance may be used in an amount of 3 moles or more, or 3 moles to 12 moles, based on 1 mole of the alcohol compound.

The reflux may be conducted at a temperature of 90° C. to 120° C. or 100° C. to 110° C. for 1 hours to 10 hours.

The step of preparing a thiouronium salt may be carried out in air or in a nitrogen atmosphere. It is preferable to be carried out in a nitrogen atmosphere from the viewpoint of color, but it is not limited thereto.

The process for preparing a polythiol composition according to an embodiment comprises adding a basic solution to the thiouronium salt solution to hydrolyze it.

The basic solution may comprise an organic base or an inorganic base. For example, it may be one or more organic bases selected from the group comprising ammonia, sodium hydroxide, potassium hydroxide, potassium phosphate, sodium carbonate, and sodium acetate; or it may be one or more inorganic bases selected from the group comprising hydrazine, and triethylamine. Specifically, the basic solution may comprise at least one selected from the group consisting of sodium hydroxide, potassium hydroxide, ammonia, potassium phosphate, sodium carbonate, and triethylamine.

According to an embodiment, the hydrolysis step may be carried out at 20° C. to 70° C. for 1 hour or longer. For example, the hydrolysis step may be carried out at 20° C. to 65° C., 25° C. to 60° C., or 30° C. to 50° C. for 1 hour or longer, 2 hours or longer, 1 to 10 hours, 1 to 9 hours, or 2 to 9 hours. The time for adding the basic solution may be adjusted in consideration of cooling facilities, equipment, and the like. If the above temperature range is satisfied when the basic solution is added, the coloring of the obtained polythiol compound does not readily occur.

The hydrolysis step may be carried out in air or in a nitrogen atmosphere. It is preferable to be carried out in a nitrogen atmosphere from the viewpoint of color, but it is not limited thereto.

According to an embodiment, the hydrolysis step is terminated when the area of peak A in the graph measured by gel permeation chromatography of the reactant in the hydrolysis step is 0.5% to 8% based on the total peak area.

Here, peak A is a peak located at −0.37 minute±0.08 minute with respect to the maximum peak (peak B) in the graph. The gel permeation chromatography is carried out under the conditions that tetrahydrofuran is used as the mobile phase, two columns are connected in series, the columns each having a length of 145 mm to 155 mm, a diameter of 4.5 mm to 4.7 mm, a pore size of 44 Å to 46 Å, and a particle size of 1.6 μm to 1.8 μm, the flow rate is 0.45 ml/minute to 0.55 ml/minute, or 0.5 ml/minute, and the injection amount is 9.5 μl to 10.5 μl, or 10 μl. The particle size of the column refers to the particle diameter.

Specifically, the column may be ACQUITY APC XT 45 of Waters.

According to an embodiment, once the basic solution is added in the hydrolysis step, a part of the reactant may be collected at intervals of 5 minutes to 15 minutes to measure GPC. For example, once the basic solution is added in the hydrolysis step, a part of the reactant may be collected at intervals of 5 minutes to 13 minutes, 5 minutes to 10 minutes, or 5 minutes to 7 minutes to measure GPC.

According to an embodiment, peak A may be at −0.37 minute±0.08 minute, −0.37 minute±0.06 minute, or −0.37 minute±0.05 minute, based on the peak (peak B) for the trifunctional polythiol compound shown in the GPC graph. The hydrolysis step is terminated when the above range is satisfied, whereby the impurities of the trifunctional polythiol compound are effectively removed, resulting in enhancements in the purity of the trifunctional polythiol compound.

According to an embodiment, the hydrolysis step may be terminated when the area of peak A is less than 5% based on the total peak area. For example, the hydrolysis step may be terminated when the area of peak A is less than 4%, or less than 3%, based on the total peak area.

According to an embodiment, the hydrolysis step may be terminated when the area of peak A is 8% or less, less than 8%, less than 6%, less than 5%, less than 3%, 0.5% to 8%, 0.5 to 6%, 0.5 to 5%, or 0.5 to 3%, based on the area of peak B.

According to an embodiment, the component of peak B may comprise a trifunctional polythiol represented by the following Formula 1:

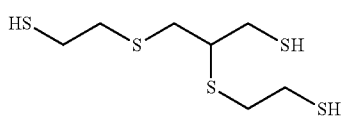

[Formula 1]

According to an embodiment, the trifunctional polythiol represented by the above Formula 1 may be 70% by weight or more based on the total weight of the polythiol composition. For example, the compound represented by the above Formula 1 may be 73% by weight or more, 75% by weight or more, 78% by weight or more, 80% by weight or to more, 83% by weight or more, or 85% by weight or more, based on the total weight of the polythiol composition.

According to an embodiment, the compound (or component) responsible for peak A may be 10% by weight or less based on the total weight of the polythiol composition. For example, the compound responsible for peak A may be less than 8% by weight, less than 7.5% by weight, or less than 7% by weight, based on the total weight of the polythiol composition.

Thereafter, if necessary, a further purification step may be carried out.

Specifically, at least one purification step selected from the group including acid washing, alkali washing, and water washing may be carried out on the polythiol composition. The purification step may be carried out repeatedly. Impurities or the like remaining in the polythiol composition can be removed through the purification step, which improves the color of the polythiol composition, resulting in enhancements in the color of the optical material produced therefrom.

Process for Preparing a Tetrafunctional Polythiol Composition

The process for preparing a tetrafunctional polythiol composition according to an embodiment comprises reacting a halogen compound or an alcohol compound with thiourea to prepare a thiouronium salt solution; and adding a basic solution to the thiouronium salt solution to hydrolyze it.

The process for preparing a polythiol composition according to an embodiment comprises reacting a halogen compound or an alcohol compound with thiourea to prepare a thiouronium salt solution.

First, in the step of preparing a thiouronium salt solution, a halogen compound and an alcohol compound are reacted to prepare a diol compound.

In this step, the alcohol compound may be reacted in an amount of 0.5 to 2 equivalents, 1 to 2 equivalents, 0.5 to 1.5 equivalents, or 0.5 to 1 equivalent, based on 1 equivalent of the halogen compound.

Here, a tertiary amine, a quaternary ammonium salt, triphenylphosphine, and a trivalent chromium compound may be used as a reaction catalyst. For example, triethylamine, triphenylphosphine, triethyl ammonium chloride, chromium (III) octoate, or the like may be used.

The catalyst may be used in an amount of 0.5 to 2 equivalents, or 0.5 to 1 equivalent, based on 1 equivalent of the halogen compound.

The halogen compound may comprise F, Cl, Br, I, and the like. For example, it may be epichlorohydrin, but it is not limited thereto. The alcohol compound may be, for example, 2-mercaptoethanol, but it is not limited thereto.

Next, the diol compound may be reacted with a metal sulfide in a solvent to prepare a tetrafunctional polyol compound. The reaction may be carried out at a temperature of 10 to 50° C., particularly 20 to 40° C., for 1 to 10 hours, 1 to 8 hours, or 1 to 5 hours. The metal sulfide may be, for example, sodium sulfide ($Na_2S$). The metal sulfide may be used in the form of an aqueous solution or solid. The metal sulfide may be used in an amount of 0.4 to 0.6 equivalent, 0.45 to 0.57 equivalent, or 0.48 to 0.55 equivalent, based on 1 equivalent of the diol compound.

Next, the tetrafunctional polyol compound may be reacted with thiourea under an acidic condition to prepare an isothiouronium salt. More specifically, the reaction may be carried out under reflux.

The thiourea may be used in an amount of 3 moles or more based on 1 mole of the alcohol compound. For example, the thiourea may be used in an amount of 3 moles to 6 moles, or 4.6 moles to 5 moles, based on 1 mole of the alcohol compound.

For the acidic condition, a hydrochloric acid solution, hydrogen chloride gas, or the like may be used. The type of the acidic substance to be used is not particularly limited as long as the reaction can be sufficiently carried out. For example, the use of hydrogen chloride may secure a sufficient reaction rate and prevent the coloring of the product. In addition, the acidic substance may be used in an amount of 3 moles or more, or 3 moles to 12 moles, based on 1 mole of the alcohol compound.

The reflux may be conducted at a temperature of 90° C. to 120° C. or 100° C. to 110° C. for 1 hours to 10 hours.

The step of preparing a thiouronium salt may be carried out in air or in a nitrogen atmosphere. It is preferable to be carried out in a nitrogen atmosphere from the viewpoint of color, but it is not limited thereto.

The process for preparing a polythiol composition according to an embodiment comprises adding a basic solution to the thiouronium salt solution to hydrolyze it.

The basic solution may comprise an organic base or an inorganic base. For example, it may be one or more organic bases selected from the group comprising ammonia, sodium hydroxide, potassium hydroxide, potassium phosphate, sodium carbonate, and sodium acetate; or it may be one or more inorganic bases selected from the group comprising hydrazine, and triethylamine. Specifically, the basic solution may comprise at least one selected from the group consisting of sodium hydroxide, potassium hydroxide, ammonia, potassium phosphate, sodium carbonate, and triethylamine.

According to an embodiment, the hydrolysis step may be carried out at 20° C. to 70° C. for 1 hour or longer. For example, the hydrolysis step may be carried out at 20° C. to 65° C., 25° C. to 60° C., or 30° C. to 50° C. for 1 hour or longer, 2 hours or longer, 1 to 10 hours, 1 to 9 hours, or 2 to 9 hours. The time for adding the basic solution may be adjusted in consideration of cooling facilities, equipment, and the like. If the above temperature range is satisfied when the basic solution is added, the coloring of the obtained polythiol compound does not readily occur.

The hydrolysis step may be carried out in air or in a nitrogen atmosphere. It is preferable to be carried out in a nitrogen atmosphere from the viewpoint of color, but it is not limited thereto.

According to an embodiment, the hydrolysis step may be terminated when the area of peak C in the graph measured by gel permeation chromatography of the reactant in the hydrolysis step is 0.5% to 8% based on the total peak area.

Here, peak C is a peak located at −0.4 minute±0.15 minute with respect to the maximum peak (peak D) in the graph. The gel permeation chromatography is carried out under the conditions that tetrahydrofuran is used as the mobile phase, two columns are connected in series, the columns each having a length of 145 mm to 155 mm, a diameter of 4.5 mm to 4.7 mm, a pore size of 44 Å to 46 Å, and a particle size of 1.6 μm to 1.8 μm, the flow rate is 0.45 ml/minute to 0.55 ml/minute, or 0.5 ml/minute, and the injection amount is 9.5 μl to 10.5 μl, or 10 μl. The particle size of the column refers to the particle diameter.

Specifically, the column may be ACQUITY APC XT 45 of Waters.

According to an embodiment, once the basic solution is added in the hydrolysis step, a part of the reactant may be collected at intervals of 5 minutes to 15 minutes to be measured by the GPC. For example, once the basic solution is added in the hydrolysis step, a part of the reactant may be collected at intervals of 5 minutes to 13 minutes, 5 minutes to 10 minutes, or 5 minutes to 7 minutes to be measured by the GPC.

According to an embodiment, peak C may be at −0.4 minute±0.15 minute, −0.4 minute±0.14 minute, −0.4 minute±0.13 minute, or −0.4 minute±0.10 minute, based on the peak (peak D) for the polythiol compound shown in the GPC graph. The hydrolysis step is terminated when the above range is satisfied, whereby the impurities of the tetrafunctional polythiol compound are effectively removed, resulting in enhancements in the purity of the tetrafunctional polythiol compound.

According to an embodiment, the hydrolysis step may be terminated when the area of peak C is less than 5% based on the total peak area. For example, the hydrolysis step may be terminated when the area of peak C is less than 4%, or less than 3%, based on the total peak area.

According to an embodiment, the hydrolysis step may be terminated when the area of peak C is 10% or less, less than 10%, 8% or less, less than 8%, less than 6%, less than 5%, less than 3%, 0.5% to 10%, 0.5 to 8%, 0.5 to 6%, 0.5 to 5%, or 0.5 to 3%, based on the area of peak D.

According to an embodiment, the component of peak D may comprise a tetrafunctional polythiol represented by the following Formula 2:

[Formula 2]

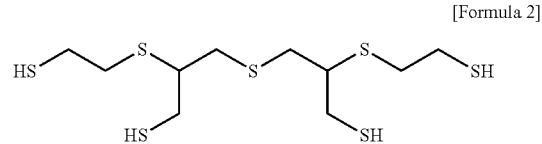 [SMILES: SCCSC(CS)CSCC(CS)SCCS]

According to an embodiment, the tetrafunctional polythiol represented by the above Formula 2 may be 70% by weight or more based on the total weight of the polythiol composition. For example, the compound represented by the above Formula 2 may be 73% by weight or more, 75% by weight or more, 78% by weight or more, 80% by weight or more, 83% by weight or more, or 85% by weight or more, based on the total weight of the polythiol composition.

According to an embodiment, the compound (or component) responsible for peak C may be 10% by weight or less based on the total weight of the polythiol composition. For example, the compound responsible for peak C may be less than 8% by weight, less than 7.5% by weight, or less than 7% by weight, based on the total weight of the polythiol composition.

Thereafter, if necessary, a further purification step may be carried out. The purification step is the same as described in the process for preparing a trifunctional polythiol composition. Impurities or the like remaining in the polythiol composition can be removed through the purification step, which improves the color of the polythiol composition, resulting in enhancements in the color of the optical material produced therefrom.

Polythiol Composition

The present invention is capable of providing a polythiol composition comprising a trifunctional polythiol compound with high purity and a polythiol composition comprising a tetrafunctional polythiol compound with high purity.

Trifunctional Polythiol Composition

The polythiol composition according to an embodiment comprises a polythiol represented by the following Formula 1, wherein the area of peak A in the graph measured by gel permeation chromatography of the entire composition is 0.5% to 8% based on the total peak area:

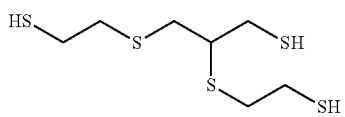

[Formula 1]

Here, peak A is a peak located at −0.37 minute±0.08 minute with respect to the maximum peak (peak B) in the graph. The conditions for the gel permeation chromatography are as described above.

According to an embodiment, the polythiol composition may have an APHA (American Public Health Association) value of less than 20, 15 or less, 13 or less, 10 or less, 7 or less, or 5 or less, according to the JIS-K-0071-1 standard.

According to an embodiment, the polythiol composition may have a color coordinate b* value of 1.0 or less, 0.9 or less, 0.8 or less, 0.7 or less, 0.6 or less, 0.5 or less, or 0.4 or less.

Tetrafunctional Polythiol Composition

The polythiol composition according to an embodiment comprises a tetrafunctional polythiol represented by the following Formula 2, wherein the area of peak C in the graph measured by gel permeation chromatography of the entire composition is 0.5% to 8% based on the total peak area:

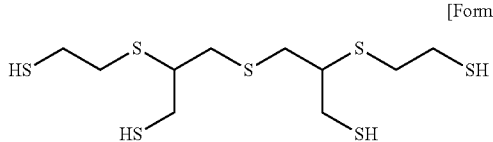

[Formula 2]

Here, peak C is a peak located at −0.4 minute±0.15 minute with respect to the maximum peak (peak D) in the graph. The conditions for the gel permeation chromatography are as described above.

According to an embodiment, the polythiol composition may have an APHA (American Public Health Association) value of less than 20, 15 or less, 13 or less, 10 or less, or less, according to the JIS-K-0071-1 standard.

According to an embodiment, the polythiol composition may have a color coordinate b* value of 1.0 or less, 0.9 or less, 0.8 or less, 0.7 or less, 0.6 or less, or 0.55 or less.

Polymerizable Composition

The polymerizable composition according to an embodiment comprises a polythiol composition; and an isocyanate-based compound, wherein the polythiol composition comprises a trifunctional polythiol represented by the above Formula 1, wherein the area of peak A in the graph measured by gel permeation chromatography of the polythiol composition is 0.5% to 8% based on the total peak area. Here, peak A is a peak located at −0.37 minute±0.08 minute with respect to the maximum peak (peak B) in the graph. The conditions for the gel permeation chromatography are as described above.

The polymerizable composition according to an embodiment comprises a polythiol composition; and an isocyanate-based compound, wherein the polythiol composition comprises a tetrafunctional polythiol represented by the above Formula 2, wherein the area of peak C in the graph measured by gel permeation chromatography of the polythiol composition is 0.5% to 8% based on the total peak area. Here, peak C is a peak located at −0.4 minute±0.15 minute with respect to the maximum peak (peak D) in the graph. The conditions for the gel permeation chromatography are as described above.

The polymerizable composition may comprise one to five types, one to three types, two types, or one type of a bifunctional or trifunctional isocyanate compound.

For example, the isocyanate compound may comprise at least one selected from the group consisting of an aliphatic isocyanate compound such as isophorone diisocyanate, dicyclohexylmethane-4,4-diisocyanate, hexamethylene diisocyanate, 2,2-dimethylpentane diisocyanate, 2,2,4-trimethylhexane diisocyanate, butene diisocyanate, 1,3-butadiene-1,4-diisocyanate, 2,4,4-trimethylhexamethylene diisocyanate, 1,6,11-undecatriisocyanate, 1,3,6-hexamethylene triisocyanate, 1,8-diisocyanate-4-isocyanatomethyloctane, bis(isocyanatoethyl)carbonate, and bis(isocyanatoethyl) ether; an alicyclic isocyanate compound such as isophorone diisocyanate, 1,2-bis(isocyanatomethyl)cyclohexane, 1,3-bis(isocyanatomethyl)cyclohexane, 1,4-bis(isocyanatomethyl)cyclohexane, dicyclohexylmethane diisocyanate, cyclohexane diisocyanate, methylcyclohexane diisocyanate, dicyclohexyldimethylmethane isocyanate, 2,2-dimethyldicyclohexylmethane isocyanate, and norbornane diisocyanate; and an aromatic isocyanate compound such as bis(isocyanatomethyl)benzene, bis(isocyanatoethyl)benzene, bis(isocyanatopropyl)benzene, bis(isocyanatobutyl)benzene, bis(isocyanatomethyl)naphthalene, bis(isocyanatomethyl)diphenyl ether, phenylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, toluidine diisocyanate, 4,4-diphenylmethane diisocyanate, 3,3-dimethyldiphenylmethane-4,4-diisocyanate, bibenzyl-4,4-diisocyanate, bis(isocyanatophenyl)ethylene, 3,3-dimethoxybiphenyl-4,4-diisocyanate, hexahydrobenzene diisocyanate, hexahydrodiphenylmethane-4,4-diisocyanate, o-xylylene diisocyanate, m-xylylene diisocyanate, p-xylylene diisocyanate, and toluene diisocyanate; a sulfur-containing aliphatic isocyanate compound such as bis(isocyanatoethyl) sulfide, bis(isocyanatopropyl) sulfide, bis(isocyanatohexyl) sulfide, bis(isocyanatomethyl) sulfone, bis(isocyanatomethyl) disulfide, bis(isocyanatopropyl) disulfide, bis(isocyanatomethylthio)methane, bis(isocyanatoethylthio)methane, bis(isocyanatoethylthio)ethane, bis(isocyanatomethylthio)ethane, and 1,5-diisocyanato-2-isocyanatomethyl-3-thiapentane; a sulfur-containing aromatic isocyanate compound such as diphenyl disulfide-2,4-diisocyanate, diphenyl disulfide-4,4-diisocyanate, 3,3-dimethoxy-4,4-diisocyanatodibenzylthio ether, bis(4-isocyanatomethylbenzene) sulfide, 4,4-methoxybenzenethioethylene glycol-3,3-diisocyanate, diphenyl disulfide-4,4-diisocyanate, 2,2-dimethyldiphenyl disulfide-5,5-diisocyanate, 3,3-dimethyldiphenyl disulfide-5,5-diisocyanate, 3,3-dimethyldiphenyl disulfide-6,6-diisocyanate, 4,4-dimethyldiphenyl disulfide-5,5-diisocyanate, 3,3-dimethoxydiphenyl disulfide-4,4-diisocyanate, and 4,4-dimethoxydiphenyl disulfide-3,3-diisocyanate; and a sulfur-containing heterocyclic isocyanate compound such as 2,5-diisocyanatothiophene, 2,5-bis(isocyanatomethyl)thiophene, 2,5-diisocyanatotetrahydrothiophene, 2,5-bis(isocyanatomethyl)tetrahydrothiophene, 3,4-bis(isocyanatomethyl)tetrahydrothiophene, 2,5-diisocyanato-1,4-dithiane, 2,5-bis(isocyanatomethyl)-1,4-dithiane, 4,5-diisocyanato-1,3-dithiolane, 4,5-bis(isocyanatomethyl)-1,3- dithiolane, and 4,5-bis(isocyanatomethyl)-2-methyl-1,3-dithiolane. Specifically, the isocyanate compound may be one to five selected from the group consisting of isophorone diisocyanate, norbornane diisocyanate, m-xylylene diisocyanate, toluene diisocyanate, hexamethylene diisocyanate, and cyclohexane diisocyanate, but it is not limited thereto.

The weight average molecular weight of the isocyanate compound may be 100 g/mole to 900 g/mole or 150 g/mole to 800 g/mole.

The polymerizable composition may comprise the polythiol compound and the isocyanate compound at a molar ratio of 0.5 to 1.5:1 or 0.8 to 1.2:1.

The polymerizable composition may further comprise a catalyst. Specifically, the catalyst may be at least one selected from the group consisting of dibutyltin dichloride, dimethyltin dichloride, diethyltin dichloride, dipropyltin dichloride, di-isopropyltin dichloride, and di-tert-butyltin dichloride.

The polymerizable composition may further comprise such additives as an internal mold release agent, a polymerization initiator, a thermal stabilizer, an ultraviolet absorber, a blueing agent, a chain extender, a crosslinking agent, a light stabilizer, an antioxidant, and a filler, depending on the purpose thereof.

For example, the internal mold release agent may comprise at least one selected from the group consisting of a fluorine-based nonionic surfactant having a perfluoroalkyl group, a hydroxyalkyl group, or a phosphate ester group; a silicone-based nonionic surfactant having a dimethylpolysiloxane group, a hydroxyalkyl group, or a phosphate ester group; an alkyl quaternary ammonium salt such as trimethylcetylammonium salt, trimethylstearylammonium salt, dimethylethylcetylammonium salt, triethyldodecylammonium salt, trioctylmethylammonium salt, and diethylcyclohexadodecylammonium salt; and an acidic phosphate ester.

The polymerization initiator may include, for example, an amine type, a phosphorus type, an organotin type, an organic copper type, an organic gallium type, an organic zirconium type, an organic iron type, an organic zinc, and an organic aluminum.

The thermal stabilizer may include, for example, a metal fatty acid salt type, a phosphorus type, a lead type, or an organotin type.

As the ultraviolet absorber, benzophenone-based, benzotriazole-based, salicylate-based, cyanoacrylate-based, oxanilide-based, or the like may be used.

The blueing agent has an absorption band in the wavelength range from orange to yellow in the visible light region and has a function of adjusting the color of an optical material made of a resin. Specifically, the blueing agent may comprise a material that exhibits blue to violet color, but it is not particularly limited thereto. In addition, examples of the blueing agent include a dye, a fluorescent whitening agent, a fluorescent pigment, and an inorganic pigment. It may be properly selected in accordance with the properties required for an optical component to be produced and the resin color. The blueing agent may be used alone or in combination of two or more. In view of the solubility in the polymerizable composition and the transparency of the optical material to be produced, a dye is preferably used as the bluing agent. From the viewpoint of the absorption wavelength, the dye may particularly have a maximum absorption wavelength of 520 to 600 nm; and more particularly, it may have a maximum absorption wavelength of 540 to 580 nm. In addition, in terms of the structure of the compound, an anthraquinone-based dye is preferable as the dye. The method of adding the blueing agent is not particularly limited, and the blueing agent may be added to the monomers in advance. Specifically, various methods can be used; for example, the blueing agent may be dissolved in the monomers or may be contained in a master solution in a high concentration, the master solution being later diluted with the monomers or other additives and then added.

The polymerizable composition may have a viscosity of 1,000 cps or more after it stands at 10° C. for 24 hours. Specifically, the polymerizable composition may have a viscosity of 1,000 cps to 10,000 cps or 1,500 cps to 10,000 cps after it stands at 10° C. for 24 hours. If the viscosity of the polymerizable composition after it stands at 10° C. for 24 hours is within the above range, it is possible to prevent the problem that the reactivity of the composition is too high, which lowers the workability, or that the reactivity of the composition is too low, which lowers the production yield.

When the polymerizable composition is made into a specimen having a diameter of 75 mm and a thickness of 10 mm, it may have a generation rate of bubbles of 0% to 10%. Specifically, when the polymerizable composition is made into a specimen having a diameter of 75 mm and a thickness of 10 mm, it may have a generation rate of bubbles of 0% to 8% or 0% to 5%.

Optical Material

The optical lens according to an embodiment is prepared by thermally curing the polymerizable composition.

Specifically, the optical material may be comprised of a molded article prepared by curing the polymerizable composition. In addition, the optical material may be produced by polymerizing and molding the polymerizable composition.

The optical material may comprise a polythiourethane-based polymer obtained by polymerizing (and curing) a polymerizable composition comprising a trifunctional or tetrafunctional polythiol composition according to the embodiment, and a polyisocyanate compound. The reaction molar ratio of SH groups to NCO groups in the polymerization reaction may be 0.5 to 3.0, particularly 0.6 to 2.0 or 0.8 to 1.3. Within the above range, it is possible to enhance such properties as refractive index and thermal resistance required for an optical material and the balance between them.

According to an embodiment, the optical material obtained from the trifunctional polythiol composition may have a solid-phase refractive index of greater than 1.63 to less than 1.71. For example, the solid-phase refractive index of the optical material may be 1.64 to 1.70 or 1.65 to 1.69.

According to an embodiment, the optical material obtained from the trifunctional polythiol composition may have a yellow index (Y.I.) of less than 23.0. For example, the yellow index (Y.I.) of the optical material may be 15.0 to 23.0, 15.0 to 22.0, 15.0 to 21.0, 15.0 to 20.0, 15.0 to 19.0, or 15.0 to 18.0.

According to an embodiment, the optical material obtained from the tetrafunctional polythiol composition may have a solid-phase refractive index of greater than 1.63 to less than 1.71. For example, the solid-phase refractive index of the optical material may be 1.64 to 1.70 or 1.65 to 1.69.

According to an embodiment, the optical material obtained from the tetrafunctional polythiol composition may have a yellow index (Y.I.) of less than 23.0. For example, the yellow index (Y.I.) of the optical material may be 15.0 to 23.0, 15.0 to 22.0, 15.0 to 21.0, 15.0 to 20.0, 15.0 to 19.0, 15.0 to 18.0, or 16.0 to 18.0.

The optical material may be an optical lens. More specifically, the optical material may be a plastic optical lens. In addition, the optical material may have various shapes by changing the mold used in the production thereof. Specifically, the optical material may be in the form of an eyeglass lens, a camera lens, a light emitting diode (LED), or the like.

According to an embodiment, there is provided a process for preparing an optical material from the polymerizable composition. Specifically, the process may comprise injecting the polymerizable composition into a mold and then thermally curing it.

Specifically, the optical material may be comprised of a molded article prepared by thermally curing the polymerizable composition. In addition, the optical material may be produced by polymerizing and molding the polymerizable composition.

First, the polymerizable composition is degassed under a reduced pressure and then injected into a mold for molding an optical material. Such degassing and mold injection may be carried out in a temperature range of, for example, 5 to 40° C. Specifically, it may be carried out in a temperature range of 5 to 20° C. Once the composition is injected into the mold, polymerization is usually carried out by gradually heating the composition from a low temperature to a high temperature. The temperature of the polymerization reaction may be, for example, 5 to 200° C., particularly 10 to 150° C. In addition, a reaction catalyst, which is conventionally used in the production of polythiourethane, may be employed in order to control the reaction rate. Specific examples of the reaction catalyst are as exemplified above.

Then, the polythiourethane-based optical material is released from the mold.

The optical material may have various shapes by changing the mold used in the production thereof.

The specific form and physical properties of the optical material prepared from the above process are as described below.

Mode for Carrying out the Invention

Hereinafter, the present invention will be described in detail with reference to the embodiments. The embodiments may be modified into various forms as long as the gist of the invention is not altered.

Example 1

<Preparation of a Trifunctional Polythiol Composition>

A reactor was charged with 200 parts by weight of 2-mercaptoethanol, 200 parts by weight of degassed water (dissolved oxygen concentration of 2 ppm), and 61.4 parts by weight of sodium hydroxide, which were mixed. 118.4 parts by weight of epichlorohydrin was slowly added dropwise at 9° C. to 13° C., followed by stirring thereof for 3 hours. Thereafter, 360.5 parts by weight of thiourea and 666.8 parts by weight of hydrochloric acid having a purity of 36% were added to the reactor. It was stirred at 110° C. under reflux for 3 hours for the reaction to produce a thiouronium salt. The reactor was cooled to 45° C., 589.7 parts by weight of toluene was added, and it was cooled to 26° C. Next, hydrolysis was carried out while 829 parts by weight of sodium hydroxide of 33% by weight was slowly added dropwise and gel permeation chromatography (GPC) according to the following conditions was checked. Here, the hydrolysis was terminated when the area of peak A at −0.37 minute±0.08 minute with respect to the peak (peak B) for the trifunctional polythiol compound was less than 8% based on the total peak area.

Thereafter, 234 parts by weight of 36% hydrochloric acid was added for washing at 33 to 40° C. for 30 minutes. Next, 530 parts by weight of degassed water (dissolved oxygen concentration of 2 ppm) was added for washing four times at 35 to 45° C. for 30 minutes. Then, toluene and a minute amount of water were removed under heating and depressurization, and it was filtered under reduced pressure with a PTFE type membrane filter to obtain 250 parts by weight of a polythiol composition containing a trifunctional polythiol compound as a main component.

<Gpc Conditions>
Instrument: Waters APC system
Column: Acquity APC XT Column 45 (diameter 4.6 mm, length 150 mm)
The two columns were connected in series
Mobile phase: tetrahydrofuran (THF)
Flow rate: 0.5 ml/minute
Total measurement time: 10 minutes
Injection volume: 10 µl
Detector: RID (Refractive Index Detector, 40° C.)

FIG. 1 is a graph obtained by performing GPC on the polythiol composition of Example 1.

Table 1 below shows the peak results at the time of termination of the hydrolysis in Example 1.

TABLE 1

| RT (min) | Area | Height | % Area |
|---|---|---|---|
| 4.973 | 12,237 | 1,697 | 0.81 |
| 5.056 | 24,374 | 4,014 | 1.61 (Peak A) |
| 5.152 | 24,483 | 3,789 | 1.62 |
| 5.308 | 96,465 | 25,760 | 6.38 |
| 5.426 | 1,289,188 | 362,908 | 85.21 (Peak B) |
| 5.547 | 66,282 | 12,078 | 4.38 |

As can be seen from Table 1 above, in Example 1, the hydrolysis was terminated when the area of peak A at −0.37 minute±0.08 minute with respect to the peak (peak B) for the trifunctional polythiol compound was less than 8%, i.e., 1.61%, based on the total peak area.

<Preparation of an Optical Material>

49.6 parts by weight of the polythiol composition prepared above, 50.4 parts by weight of m-xylylene diisocyanate, 0.01 parts by weight of dibutyltin dichloride, and 0.1 parts by weight of a phosphate ester release agent (ZELEC® UN Stepan) were homogeneously mixed, and a defoaming step was carried out at 600 Pa for 1 hour. Thereafter, it was filtered through a 3-µm Teflon filter and injected into a mold made of a glass mold and a tape. Thereafter, the mold was slowly heated from 25° C. to 120° C. at a rate of 5° C./min, and polymerization was carried out at 120° C. for 18 hours. Thereafter, it was released from the mold and further cured at 120° C. for 4 hours to prepare a specimen of the lens.

Example 2

In consideration of the error range, the experiment was carried out once again in the same manner as in Example 1.

FIG. 2 is a graph obtained by performing gel permeation chromatography on the polythiol composition of Example 2.

Table 2 below shows the peak results at the time of termination of the hydrolysis in Example 2.

TABLE 2

| RT (min) | Area | Height | % Area |
|---|---|---|---|
| 5.031 | 95,569 | 11,912 | 2.76 (Peak A) |
| 5.296 | 95,716 | 28,267 | 2.76 |
| 5.415 | 3,147,488 | 833,062 | 90.81 (Peak B) |
| 5.535 | 127,228 | 24,305 | 3.67 |

As can be seen from Table 2 above, in Example 2, the hydrolysis was terminated when the area of peak A at −0.37 minute±0.08 minute with respect to the peak (peak B) for the trifunctional polythiol compound was less than 8%, i.e., 2.76%, based on the total peak area.

Comparative Example 1

An experiment was carried out in the same manner as in Example 1, except that the hydrolysis was terminated when the area of peak A at −0.37 minute±0.08 minute with respect to the peak (peak B) for the trifunctional polythiol compound exceeded 8% based on the total peak area.

Table 3 below shows the peak results at the time of termination of the hydrolysis in Comparative Example 1.

TABLE 3

| RT (min) | Area | Height | % Area |
| --- | --- | --- | --- |
| 4.781 | 25,074 | 3058 | 1.62 |
| 5.033 | 141,231 | 32302 | 9.11 (Peak A) |
| 5.302 | 95,526 | 13331 | 6.16 |
| 5.417 | 1,218,884 | 362908 | 78.64 (Peak B) |
| 5.594 | 69,224 | 10480 | 4.47 |

As can be seen from Table above, in Comparative Example, the hydrolysis was terminated when the area of peak A at −0.37 minute±0.08 minute with respect to the peak (peak B) for the trifunctional polythiol compound exceeded 8%, i.e., 9.11%, based on the total peak area.

Comparative Example 2

An experiment was carried out in the same manner as in Example 1, except that the hydrolysis was terminated when the area of peak A at −0.37 minute±0.08 minute with respect to the peak (peak B) for the trifunctional polythiol compound was less than 0.5% based on the total peak area.

Table 4 below shows the peak results at the time of termination of the hydrolysis in Comparative Example 2.

TABLE 4

| RT (min) | Area | Height | % Area |
| --- | --- | --- | --- |
| 4.799 | 16,522 | 16,522 | 2.91 |
| 5.025 | 1,860 | 1,860 | 0.35 (Peak A) |
| 5.288 | 2,122 | 2,122 | 0.23 |
| 5.412 | 845,544 | 845,544 | 91.82 (Peak B) |
| 5.549 | 45,516 | 45,516 | 4.69 |

As can be seen from Table 4 above, in Comparative Example 2, the hydrolysis was terminated when the area of peak A at −0.37 minute±0.08 minute with respect to the peak (peak B) for the trifunctional polythiol compound was less than 0.5%, i.e., 0.35%, based on the total peak area. Here, the time for hydrolysis was about 8 hours or more.

Example 3

<Preparation of a Tetrafunctional Polythiol Composition>

A reactor was charged with 43.0 parts by weight of water, 1.3 parts by weight of triethylamine, and 73.0 parts by weight of 2-mercaptoethanol, followed by lowering the temperature to 0° C. Thereafter, 88.0 parts by weight of epichlorohydrin was slowly added dropwise at 15° C. or lower, followed by stirring thereof for 1 hour at 30° C. Thereafter, 145.0 parts by weight of an aqueous solution of 25% sodium sulfide was slowly added thereto dropwise at 20° C. to 25° C., followed by stirring thereof for 3 hours.

Thereafter, 245.0 parts by weight of 36% hydrochloric acid and 149.0 parts by weight of thiourea were added, followed by stirring thereof for 3 hours with reflux at 110° C. for the reaction to produce a thiouronium salt.

Thereafter, after it was cooled to 50° C., hydrolysis was carried out while 200.0 parts by weight of toluene and 280.0 parts by weight of 40% sodium hydroxide were slowly added dropwise and gel permeation chromatography (GPC) was checked. Here, the hydrolysis was terminated when the area of peak C at −0.4 minute±0.15 minute with respect to the peak (peak D) for the tetrafunctional polythiol compound was less than 10% based on the total peak area.

Thereafter, washing was carried out once at 33° C. to 40° C. for 30 minutes with a toluene solution to which 120 parts by weight of 36% hydrochloric acid had been added. Thereafter, 200 parts by weight of degassed water (dissolved oxygen concentration of 2 ppm) was added for washing four times at 35° C. to 45° C. for 30 minutes. Toluene and a minute amount of water were removed under heating and depressurization, and it was filtered under reduced pressure with a PTFE type membrane filter to obtain 125 parts by weight of a polythiol composition containing a tetrafunctional polythiol compound as a main component. The GPC conditions are the same as above.

FIG. 3 is a graph obtained by performing GPC on the polythiol composition of Example 3.

Table 5 below shows the peak results at the time of termination of the hydrolysis in Example 3.

TABLE 5

| RT (min) | Area | Height | % Area |
| --- | --- | --- | --- |
| 4.847 | 239,627 | 31,059 | 6.96 (Peak C) |
| 5.038 | 92,929 | 19,153 | 2.70 |
| 5.129 | 225,660 | 38,985 | 6.55 |
| 5.262 | 2,746,734 | 698,509 | 79.74 (Peak D) |
| 5.426 | 104,098 | 27,537 | 3.02 |
| 5.564 | 35,489 | 3,681 | 1.03 |

As can be seen from Table 5 above, in Example 3, the hydrolysis was terminated when the area of peak C at −0.4 minute±0.15 minute with respect to the peak (peak D) for the tetrafunctional polythiol compound was less than 10%, i.e., 6.96%, based on the total peak area.

<Preparation of an Optical Material>

49.3 parts by weight of the polythiol composition prepared above, 50.7 parts by weight of m-xylylene diisocyanate, 0.01 parts by weight of dibutyltin dichloride, and 0.1 parts by weight of a phosphate ester release agent (ZELEC® UN Stepan) were homogeneously mixed, and a defoaming step was carried out at 600 Pa for 1 hour. Thereafter, it was filtered through a 3-μm Teflon filter and injected into a mold made of a glass mold and a tape. Thereafter, the mold was slowly heated from 25° C. to 120° C. at a rate of 5° C./min, and polymerization was carried out at 120° C. for 18 hours. Thereafter, it was released from the mold and further cured at 120° C. for 4 hours to prepare a specimen of the lens.

Example 4

In consideration of the error range, the experiment was carried out once again in the same manner as in Example 3.

FIG. 4 is a graph obtained by performing gel permeation chromatography on the polythiol composition of Example 4.

Table 6 below shows the peak results at the time of termination of the hydrolysis in Example 4.

TABLE 6

| RT (min) | Area | Height | % Area |
|---|---|---|---|
| 5.258 | 92,873 | 12,695 | 6.31 (Peak C) |
| 5.474 | 42,959 | 8,215 | 2.92 |
| 5.608 | 53,207 | 10,987 | 3.62 |
| 5.710 | 1,216,123 | 284,828 | 82.63 (Peak D) |
| 5.889 | 42,128 | 10,495 | 2.86 |
| 6.041 | 24,450 | 3,020 | 1.66 |

As can be seen from Table 6 above, in Example 4, the hydrolysis was terminated when the area of peak C at −0.4 minute±0.15 minute with respect to the peak (peak D) for the tetrafunctional polythiol compound was less than 10%, i.e., 6.31%, based on the total peak area.

Comparative Example 3

An experiment was carried out in the same manner as in Example 3, except that the hydrolysis was terminated when the area of peak C at −0.4 minute±0.15 minute with respect to the peak (peak D) for the tetrafunctional polythiol compound exceeded 10/based on the total peak area.

Table 7 below shows the peak results at the time of termination of the hydrolysis in Comparative Example 3.

TABLE 7

| RT (min) | Area | Height | % Area |
|---|---|---|---|
| 4.890 | 136,544 | 11,910 | 2.62 |
| 5.050 | 654,281 | 78,065 | 12.53 (Peak C) |
| 5.395 | 508,360 | 6,732 | 9.74 |
| 5.492 | 3,694,611 | 750,486 | 70.76 (Peak D) |
| 5.661 | 165,874 | 36,476 | 3.18 |
| 5.805 | 61,435 | 9,365 | 1.18 |

As can be seen from Table 7 above, in Comparative Example 3, the hydrolysis was terminated when the area of peak C at −0.4 minute±0.15 minute with respect to the peak (peak D) for the tetrafunctional polythiol compound exceeded 10%, i.e., 12.53%, based on the total peak area.

Comparative Example 4

An experiment was carried out in the same manner as in Example 3, except that the hydrolysis was terminated when the area of peak C at −0.4 minute±0.15 minute with respect to the peak (peak D) for the tetrafunctional polythiol compound was less than 1% based on the total peak area.

Table 8 below shows the peak results at the time of termination of the hydrolysis in Comparative Example 4.

TABLE 8

| RT (min) | Area | Height | % Area |
|---|---|---|---|
| 5.012 | 22,486 | 3,145 | 1.56 |
| 5.215 | 12,722 | 1,739 | 0.88 (Peak C) |
| 5.459 | 36,542 | 6,988 | 2.53 |
| 5.600 | 93,198 | 19,245 | 6.45 |
| 5.699 | 1,172,115 | 274,521 | 81.14 (Peak D) |
| 5.901 | 65,257 | 16,257 | 4.52 |
| 6.033 | 42,188 | 5,211 | 2.92 |

As can be seen from Table 8 above, in Comparative Example 4, the hydrolysis was terminated when the area of peak C at −0.4 minute±0.15 minute with respect to the peak (peak D) for the tetrafunctional polythiol compound was less than 1.0%, i.e., 0.88%, based on the total peak area. Here, the time for hydrolysis in Comparative Example 4 was hours or more.

Evaluation Example 1: Evaluation of SH Values

The trifunctional polythiol compositions and the tetrafunctional polythiol compositions prepared above were each evaluated as follows.

0.1 g of the polythiol composition was placed in a beaker, and 25 ml of chloroform was added, followed by stirring the mixture for 10 minutes. Thereafter, 10 ml of methanol was added, which was stirred for 10 minutes to obtain a solution. It was titrated with 0.1 N iodine standard solution, and the SH value was then calculated by the following equation.

$SH$ value (g/eq.)=weight of sample (g)/{0.1×amount of iodine consumed (L)}

For reference, the SH value is (molecular weight of a substance)/(number of SH functional groups), which is a theoretical value that can determine the number of thiol functional groups per weight of a specific substance. However, in actual polythiols, the measured value is higher than the theoretical value due to the influence of impurities, moisture, and residual solvent. Since most impurities have a small number of SH functional groups relative to their molecular weight, the SH value increases as impurities are more contained.

Evaluation Example 2: Evaluation of Liquid-Phase Refractive Index

The trifunctional polythiol compositions and the tetrafunctional polythiol compositions prepared above were each evaluated as follows.

The refractive index of each of the polythiol compositions prepared was measured at 25° C. with a liquid-phase refractometer RA-600 of Kyoto Electronics.

Evaluation Example 3: Evaluation of Color

The trifunctional polythiol compositions and the tetrafunctional polythiol compositions prepared above were each evaluated as follows.

<Evaluation of APHA>

For each of the polythiol compositions prepared above, a standard solution was prepared in 5 units of APHA in compliance with JIS K 0071-1 standard. The APHA value of the composition was compared with the prepared standard solution with the naked eyes, and the APHA value of the most similar color was taken.

<Evaluation of b*>

The color of the polythiol composition was measured using a UV-Vis spectrophotometer (Lambda-365, PerkinElmer). Specifically, the color was measured at an interval of 1 nm in a wavelength range of 380 to 780 nm using a quartz cell (10 mm×10 mm) and a light source of D65/10°. The lower the b* value, the better the color.

Evaluation Example 4: Evaluation of Purity

The trifunctional polythiol compositions and the tetrafunctional polythiol compositions prepared above were each evaluated as follows.

The content of the trifunctional polythiol compound was measured through the peaks generated as a result of performing gel permeation chromatography on each of the trifunctional polythiol compositions prepared above. The content of the tetrafunctional polythiol compound was measured by performing the same method for each of the tetrafunctional polythiol compositions.

Evaluation Example 5: Evaluation Solid-Phase Refractive Index

The solid-phase refractive index of the lens specimen prepared above was measured at 20° C. using an Abbe refractometer DR-M4.

Evaluation Example 6: Evaluation of Stria

A stria refers to a defect in appearance caused by local phase separation due to a difference in curing rate or a difference in reaction rate while the composition is cured. The lens specimens prepared above were each observed under a mercury lamp. It was marked as ○ if there was no stria, Δ if there was a minute stria, and x if the stria was severe.

Evaluation Example 7: Evaluation of Transparency (or Cloudiness)

For the lens specimens prepared above, transparency was evaluated by checking the presence or absence of cloudiness as follows. Specifically, the lens was irradiated to a projector in a darkroom to observe whether the lens was cloudy or had any opaque material with the naked eyes. If the lens neither was cloudy nor had any opaque material, it was evaluated as ○. If it was cloudy or had any opaque material, it was evaluated as x.

Evaluation Example 8: Evaluation of Yellow Index (Y.I.)

For the lens specimens having a thickness of 9 mm and φ75 mm prepared above, chromaticity coordinates x and y were measured using a Colormate integrating sphere spectrophotometer of SCINCO to calculate the yellow index according to the following equation.

$$Y.I.=(234x+106y+106)/y$$

The results of Evaluations 1 to 8 are shown in Tables 9 and 10 below.

Table 9 shows the results of the trifunctional polythiol compositions, and Table 10 shows the results of the tetrafunctional polythiol compositions.

TABLE 9

|  | Example 1 | Example 2 | Comparative Example 1 | Comparative Example 2 |
|---|---|---|---|---|
| SH value (g/eq.) | 89.3 | 87.9 | 99.8 | 87.8 |
| Liquid-phase refractive index | 1.629 | 1.628 | 1.630 | 1.628 |
| b* | 0.52 | 0.35 | 1.1 | 1.3 |
| APHA | 10 | 5 | 20 | 25 |
| Purity | 85% | 91% | 79% | 92% |
| Solid-phase refractive index | 1.67 | 1.67 | 1.65 | 1.67 |
| Stria | ○ | ○ | x | ○ |
| Transparency | ○ | ○ | x | ○ |
| Y.I. | 17.5 | 16.6 | 19.5 | 23.5 |

TABLE 10

|  | Example 3 | Example 4 | Comparative Example 3 | Comparative Example 4 |
|---|---|---|---|---|
| SH value (g/eq.) | 97.8 | 96.8 | 99.8 | 97.0 |
| Liquid-phase refractive index | 1.647 | 1.646 | 1.649 | 1.646 |
| b* | 0.55 | 0.50 | 1.1 | 1.5 |
| APHA | 10 | 10 | 20 | 30 |
| Purity | 80% | 82% | 70% | 81% |
| Solid-phase refractive index | 1.67 | 1.67 | 1.65 | 1.67 |
| Stria | ○ | ○ | x | ○ |
| Transparency | ○ | ○ | x | ○ |
| Y.I. | 17.5 | 16.7 | 19.3 | 25.9 |

As shown in Table 9, the polythiol compositions prepared in Examples 1 and 2 had high purity of the trifunctional polythiol compound and were excellent in SH value, liquid-phase refractive index, b*, and APHA. In addition, the optical materials prepared using the same were all excellent in solid-phase refractive index, stria, transparency, and yellow index (Y.I.). In addition, in Comparative Example 2, the hydrolysis time was too long, and the performance of the lens was not enhanced; rather, it tended to be deteriorated.

In addition, as shown in Table 10, the polythiol compositions prepared in Examples 3 and 4 had high purity of the tetrafunctional polythiol compound and were excellent in SH value, liquid-phase refractive index, b*, and APHA. In addition, the optical materials prepared using the same were all excellent in solid-phase refractive index, stria, transparency, and yellow index (Y.I.). In addition, in Comparative Example 4, the hydrolysis time was too long, and the performance of the lens was not enhanced; rather, it tended to be deteriorated.

The invention claimed is:

1. A process for preparing a polythiol composition, which comprises:
    reacting a halogen compound or an alcohol compound with thiourea to prepare a thiouronium salt solution; and
    adding a basic solution to the thiouronium salt solution to hydrolyze it in a hydrolysis step,
    wherein once the basic solution is added in the hydrolysis step, a part of the reactant is collected at intervals of 5 minutes to 15 minutes to be measured by gel permeation chromatography (GPC),
    wherein the hydrolysis step is terminated when an area of peak A in the graph measured by the GPC of the reactant in the hydrolysis step is 0.5% to 8% based on the total peak area and less than 8% based on an area of peak B,
    wherein the peak A is a peak located at −0.37 minute±0.08 minute with respect to the maximum peak (peak B) in the graph,
    wherein the component of peak B comprises a trifunctional polythiol represented by the following Formula 1:

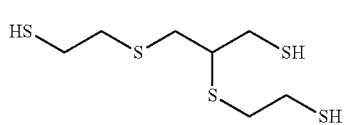

[Formula 1]

wherein the GPC is carried out under the conditions that tetrahydrofuran is used as the mobile phase, two columns are connected in series, the columns each having a length of 145 mm to 155 mm, a diameter of 4.5 mm to 4.7 mm, a pore size of 44 Å to 46 Å, and a particle diameter of 1.6 μm to 1.8 μm, the flow rate is 0.45 ml/minute to 0.55 ml/minute, and the injection amount is 9.5 μl to 10.5 μl, wherein the polythiol composition has a color coordinate b* value of 1.0 or less, and wherein APHA (American Public Health Association) value is 10 or less according to the JIS-K-0071-1 standard.

2. The process for preparing a polythiol composition of claim 1, wherein the hydrolysis step is terminated when the area of peak A is 0.5% to 5% based on the total peak area.

3. The process for preparing a polythiol composition of claim 1, wherein the trifunctional polythiol represented by the Formula 1 is 70% by weight or more based on the total weight of the polythiol composition.

4. The process for preparing a polythiol composition of claim 1, wherein the hydrolysis step is carried out at 20° C. to 70° C. for 1 hour to 9 hours.

5. A process for preparing a polythiol composition, which comprises:

reacting a halogen compound or an alcohol compound with thiourea to prepare a thiouronium salt solution; and adding a basic solution to the thiouronium salt solution to hydrolyze it in a hydrolysis step, wherein once the basic solution is added in the hydrolysis step, a part of the reactant is collected at intervals of 5 minutes to 15 minutes to be measured by gel permeation chromatography (GPC), wherein the hydrolysis step is terminated when an area of peak C in the graph measured by the GPC of the reactant in the hydrolysis step is 0.5% to 8% based on a total peak area and less than 10% based on an area of peak D, wherein the peak C is a peak located at −0.4 minute±0.15 minute with respect to the maximum peak (peak D) in the graph, wherein the component of peak D comprises a tetrafunctional polythiol represented by the following Formula 2,

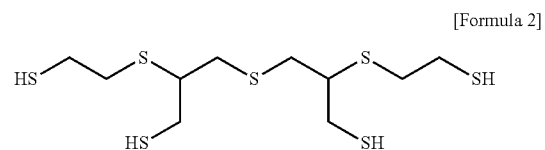 [SMILES: SCCSC(CS)CSCC(CS)SCCS]

[Formula 2]

wherein the GPC is carried out under the conditions that tetrahydrofuran is used as the mobile phase, two columns are connected in series, the columns each having a length of 145 mm to 155 mm, a diameter of 4.5 mm to 4.7 mm, a pore size of 44 Å to 46 Å, and a particle diameter of 1.6 μm to 1.8 μm, the flow rate is 0.45 ml/minute to 0.55 ml/minute, and the injection amount is 9.5 μl to 10.5 μl, and wherein the polythiol composition has a color coordinate b* value of 1.0 or less, and wherein APHA (American Public Health Association) value is 10 or less according to the JIS-K-0071-1 standard.

6. The process for preparing a polythiol composition of claim 5, wherein the hydrolysis step is terminated when the area of peak C is 1% to 8% based on the total peak area.

7. The process for preparing a polythiol composition of claim 5, wherein the tetrafunctional polythiol represented by the Formula 2 is 70% by weight or more based on the total weight of the polythiol composition.

8. The process for preparing a polythiol composition of claim 5, wherein the hydrolysis step is carried out at 20° C. to 70° C. for 1 hour to 9 hours.

* * * * *